United States Patent [19]

Maedgen, Jr.

[11] 4,260,108
[45] Apr. 7, 1981

[54] METHOD AND APPARATUS FOR AIRBORNE RELEASE OF INSECT EGGS

[75] Inventor: Malcolm A. Maedgen, Jr., Mathis, Tex.

[73] Assignee: Biogenesis, Inc., Mathis, Tex.

[21] Appl. No.: 935,923

[22] Filed: Aug. 23, 1978

[51] Int. Cl.³ .............................................. B64D 1/18
[52] U.S. Cl. .................................... 239/171; 222/161; 244/136
[58] Field of Search ................ 222/557, 161; 239/142, 239/144, 171, 394, 396, 683, 687; 138/45 A; 244/136

[56] References Cited

U.S. PATENT DOCUMENTS

| | | | |
|---|---|---|---|
| 1,982,754 | 12/1934 | Peterson | 138/45 A |
| 2,246,497 | 6/1941 | Beck | 222/161 |
| 2,356,119 | 8/1944 | Quick | 239/171 X |
| 2,986,360 | 5/1961 | Rutten | 239/171 X |
| 3,078,015 | 2/1963 | Wahl | 222/161 |
| 3,203,703 | 8/1965 | Van Der Lely et al. | 239/683 |
| 3,469,718 | 9/1969 | Felix et al. | 239/687 X |
| 3,476,337 | 11/1969 | Cornett, Jr. | 239/171 X |
| 3,484,062 | 12/1969 | Johnson | 239/171 X |
| 3,602,394 | 8/1971 | McCune | 239/142 X |

*Primary Examiner*—Robert B. Reeves
*Assistant Examiner*—Gene A. Church
*Attorney, Agent, or Firm*—Darryl M. Springs

[57] ABSTRACT

In one exemplar embodiment, method and apparatus are provided for the airborne dispensing of loose, dry insect eggs from a container by gravity flow through a metering device to control the loose egg flow to a spreader for spreading the loose eggs in a desired broadcast pattern entrained in a flow of air. A slight vacuum is applied to the container dispenser device stimulating and enhancing the steady flow of the loose eggs from the container dispenser to the spreader device.

19 Claims, 6 Drawing Figures

METHOD AND APPARATUS FOR AIRBORNE RELEASE OF INSECT EGGS

BACKGROUND OF THE INVENTION

This invention relates to methods and apparatus for airborne release and broadcast of loose insect eggs. More particularly, this invention relates to methods and apparatus for airborne release and broadcast of loose parasite/predator insect eggs for biological control of insect pests.

One of man's basic physical needs, food, has been the central core of his thoughts and efforts throughout the ages. Volume and quality, in the face of ever-increasing population and shrinking available land supply, remain a basic problem even in this advanced technological age. The raising of food crops, both as plants for consumption and as food for animals is dependent upon a number of basic life supporting elements. Adequate water is necessary, as well as means to replace nutrients removed from the soil by the plant life, and control of insect pests that feed upon the plants is a necessity. Irrigation and other water conservation measures have increased the availability of water in areas where natural rainfall is insufficient. Rotating crops and adding natural or chemical fertilizers has resolved the soil nutrient problem. But the balance and control of insect pests remains a critical and expensive problem in most parts of the world. It has been estimated by United States Department of Agriculture scientists that losses to insects in agriculture amount to thirteen percent of the production valued at over seven billion dollars annually.

Man, in his efforts to manipulate population ratios between different types of life on earth, has used various methods of control to include cultural, chemical, and natural. Each of these methods has a valid function in the overall regulatory process, but none in itself is completely curative in all circumstances. In today's world, man's efforts to control insect pests through extensive use of insecticides has led to some disconcerting effects on the agricultural economy and our ecological system.

During the post World War II days of the late 1940's and the early 1950's, scientific advances made toward increased production of food included many developments in agricultural chemicals. Some of these have proven to be highly beneficial while others have been very detrimental to our ecosystem. For example, while the use of fertilizer has increased crop yields, the use of insecticides has had (and continues to have) a very adverse effect upon our environment. Specific examples of these adverse effects can be noted as follows:

(1) the high level of tolerance to toxic compounds (insecticides) some insects have developed in recent years, calling for more frequent and heavier applications of poisons to eliminate the pest;

(2) an accumulation in the soil of non-biodegradable elements harmful to man;

(3) the absorption of these toxic elements by the plant both through the root system and through its foliage;

(4) recent medical research linking the consumption of these toxic substances through foods as a direct cause of certain types of diseases such as cancer;

(5) analysis of air and water samples by such agencies as the Environmental Protection Agency; and (6) tissue analysis of both plants and animals. According to U.S.D.A. statistics, over one billion pounds of poisons are being released into the atmosphere annually over agricultural crops.

The importance of biological control of insect pests in field crops and forests has been recognized. It has long been a part of pest management systems, and is now rising to the position of prominence in overall insect pest management it deserves.

Biological control of insect pests has many advantages in our world today when we find the environment upon which our physical life depends, degenerating from man's abuse—in a time when many of our traditional sources of energy are being depleted. It is a system of control that is self-perpeturating to the extent that the host population will support. It is a renewable resource. It fits into the overall scheme of nature as it was intended.

Because of the self-perpetuating aspect of biological control, it has a more continuous effect on insect pests. Augmentative, periodic releases of parasites and/or predators or their hosts, can be made in order to manipulate population ratios necessary in maintaining the balance of nature where problems are known to exist.

For example, a small parasitic wasp, Trichogramma, or a predator insect, Chrysopa, can be a very useful biological control agent against the Heliothis complex which has a wide range of host plants—cotton, corn, soybeans, etc. Trichogramma can also be useful in control of many Lepidopterous pests which feed upon vegetables such as tomatoes bell peppers, cabbage, collards, etc. Trichogramma can be used in combatting rice leafrollers, casebearers, and webworms. They are valuable allies in the production of many crops, and they are in no way harmful to man, livestock, or to plant life. Their life span covers an approximate seven-day period, and their life cycle is nine (9) days. Its sole purpose in life is to parasitize Lepidopterous eggs. As pupae, their nourishment is derived from the embryonic fluids of the host egg, and as an adult, its nourishment is derived from droplets of dew and nectar. While further reference herein to insect eggs shall specifically be directed to the Trichogramma parasite wasp, such reference shall include any and all other parasite and predator insects that can be useful in biological control.

Research and testing by entomologists and scientists over the world has shown that biological control of insect pests is effective, and since the Trichogramma wasp is an egg parasite native to every major agricultural producing area of the world, it is a readily available source of supply as a pest insect parasite. Research has shown that concentrations of five thousand to ten thousand Trichogramma eggs per acre can effectively control a wide variety of insect pests in their egg stage. Further, the costs of biological control are a fraction of the cost of chemical insecticides and eliminate the severe ecological side effects of such pesticides.

A basic problem, however, has been that of distribution of the parasite/predator insect eggs within the desired agricultural crop or forest in which insect pest control is desired. Originally, clusters of parasitized host eggs were carried on a small paper base, such as a one-inch paper square, using a suitable adhesive to retain the eggs on the paper carrier. Typically, such a one-inch square paper base will carry five thousand Trichogramma parasitized host eggs. The eggs and the paper base carrier were manually distributed at selected intervals throughout the desired control area. As the insect parasite eggs hatched, the insect parasites were expected to uniformly spread out over the site to be controlled and parasitize the eggs of the insect pests. However, this often did not occur and if other predators found the concentrated insect egg colony on the paper carrier before the eggs hatched, a large percentage or all of the insect parasites may be destroyed, thus leaving a large "gap" in the area coverage.

Manual distribution by a man on the ground is expensive and time-consuming, and faster techniques were sought. Another technique developed was to place the paper square carrying the insect parasite eggs in a suitable container, such as a paper cup, which was then dropped from a low-flying aircraft at the desired intervals over the site to be controlled. Although faster, the technique still suffered from the disadvantages mentioned above regarding predation and non-uniformity of distribution.

Other attempts have been made to attach the parasite insect eggs, using a suitable adhesive, to granular or flaky materials such as bran flakes and to disperse such materials from an aircraft over the desired site to achieve a more uniform distribution of the eggs. However, this technique also suffers from several disadvantages:

(1) the process of adhering the eggs to the loose material is an additional process step, thus increasing the cost;

(2) the carrier material is bulky and limits the amount of egg laden carrier that can be conveniently carried by small aircraft suitable for such airborne distribution;

(3) complex metering and distribution apparatus is necessary to control the flow of the carrier material in airborne distribution; and (4) since a large quantity of eggs are typically carried on each grain or flake of carrier material, problems of predation of a sizable percentage of the eggs still remains, particularly when coupled with the increased probability that the birds and other small animals will be attracted to and eat the carrier if it is a granular edible material such as bran or bran flakes.

It has been discovered that loose, dry parasite insect eggs can be effectively and uniformly distributed by airborne techniques utilizing the present methods and apparatus.

Accordingly, one primary feature of the present invention is to provide novel method and apparatus for uniform airborne distribution of loose, dry parasite insect eggs.

Another feature of the present invention is to provide novel method and apparatus for uniform airborne distribution of parasite insect eggs that eliminates the need for a carrier medium.

Yet another feature of the present invention is to provide methods and apparatus for airborne distribution of parasite insect eggs that requires only low-cost, lightweight and simple airborne dispensing and spreading equipment.

Still another feature of the present invention is to provide methods and apparatus for airborne distribution of parasite insect eggs that eliminates the need for large, bulky storage of carrier material.

SUMMARY OF THE INVENTION

The present invention remedies the problems of the prior art by providing methods and apparatus for releasing loose insect eggs from an aircraft or other vehicles, the broad apparatus comprising a dispensing apparatus or means located within the aircraft or vehicle for carrying and dispensing the loose insect eggs, and an air flow actuated spreading means mounted external to the aircraft or vehicle and interconnected to the dispensing apparatus to receive the flow of loose insect eggs for broadcasting the eggs in the air over the site to be controlled. In one particular embodiment, the apparatus comprises a container means for receiving the loose insect eggs and dispensing the eggs through an outlet, a metering means cooperating with the container means outlet for selectively metering the flow of the loose eggs from the container, flow enhancing means cooperating with the outlet of the container for stimulating flow of the loose eggs through the container outlet, and spreading means cooperating with the flow enhancing means for receiving the flow of loose eggs for airborne broadcast spreading of the loose eggs.

The container can conveniently be a container having a top opening and a downwardly sloping conical bottom section having an outlet in the depending apex of the bottom section. An agitating means may be employed with the container to agitate the loose eggs in the container to aid in gravity feed of the eggs through the outlet and to prevent sticking of the eggs to the container walls. One means of accomplishing such agitation is to drive a horizontal shaft disposed through the container by means of a small electric motor and reduction gearbox. The shaft carried a circular brush whose long flexible bristles rotate through the loose eggs to agitate and stir the eggs.

The metering means can conveniently take the form of a metering plate having a plurality of spaced, differing-size orifices for selectively registering the desired orifice with the outlet of the egg dispensing container to vary the flow rate of the loose eggs from the container. The spreader may conveniently be a "fan-shaped" or generally triangular-shaped vessel having an outlet that is generally in the configuration of an elongated horizontal slot and a restricted apex or opening spaced from the outlet slot. Air flow from the moving aircraft is directed through an air intake manifold that has a large intake opening and a restricted outlet opening for increasing the velocity of the air flow from the outlet. The increased velocity air flow is then applied to a short venturi section the output of which directs the high velocity air into the spreader vessel through its restricted output opening. A radial opening in the side of the venturi section is connected to the outlet of the container means for directing the loose insect eggs to the spreader. The high velocity air flow within the venturi section creates a reduction in air pressure below atmospheric, and this partial vacuum stimulates and enhances the flow of the loose insect eggs from the dispensing apparatus to the venturi section where the loose eggs are entrained with the air flow and blown into the spreader section. The "fan-shaped" spreader rapidly increases the cross-sectional area through which the air flow is directed, thus lowering its velocity and facilitating the exhaust of the air and entrained loose insect eggs in a broad swath from the spreader exhaust slot. Vertical deflection fans may be disposed along the exhaust slot of the spreader to control the air exhaust pattern.

BRIEF DESCRIPTION OF THE DRAWINGS

In order that the manner in which the above-recited advantages and features of the invention are obtained can be understood in detail, a more particular description of the invention may be had by reference to specific embodiments thereof which are illustrated in the appended drawings, which drawings form a part of this specification. It is to be noted, however, that the appended drawings illustrate only typical embodiments of the invention and therefore are not to be considered limiting of its scope for the invention may admit to further equally effective embodiments.

In the drawings.

DETAILED DESCRIPTION OF THE PREFERRED EMBODIMENT

Figure 1:
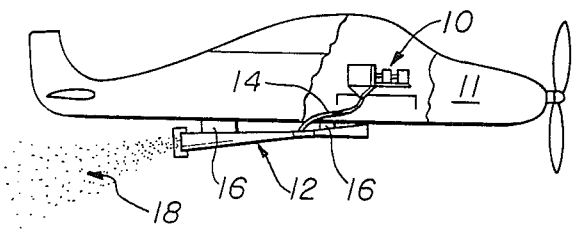
FIG. 1 is a pictorial drawing of an aircraft showing the loose egg spreading invention mounted thereon.

Referring now to FIG. 1, an aircraft 11 is shown with the loose insect egg spreading mechanism mounted thereon. The dispensing apparatus 10 is mounted within the aircraft for operation and manipulation by the pilot and/or crew, while the air actuated spreader 12 is mounted under to the fuselage of plane 11 by means of bracket 16 to orient the axis of spreader 12 along the longitudinal axis of the aircraft 11. Loose insect eggs 18 are broadcast in a desired pattern from the outlet of spreader 12. Dispensing apparatus 10 is connected to the spreader by means of a tubing 14. Details of the operation of the dispensing apparatus and the spreader will be hereinafter discussed in greater detail.

Figure 2A:
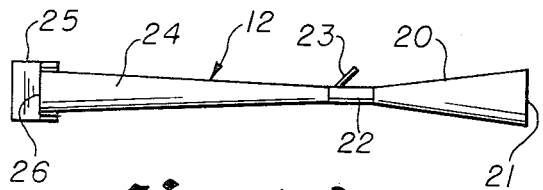
FIG. 2A is a side view of the air powered spreader that is mounted to the fuselage of the aircraft.
Figure 2B:
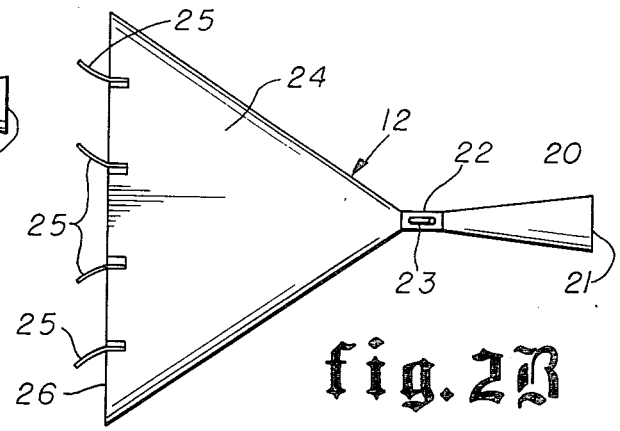
FIG. 2B is a top view of the spreader as shown in FIG. 2A.

Referring now to FIGS. 2A and 2B, the air-actuated spreader is shown. The spreader is comprised of three basic sections, an air intake manifold 20, a venturi section 22 and an exhaust or deflection duct section 24. The air intake manifold 20 is preferably conically shaped, having a large open end 21 that tapers to a much more restricted outlet opening that is fixed to the input end of venturi section 22. Manifold section 20, shown in its orientation with regard to aircraft 11 in FIG. 1, acts as an air scoop to force air flow through the large open end 21 and create a funneling effect to force the air flow through the more restricted end and into venturi section 22.

Venturi section 22 is simply a cylindrical section having a restricted cross-sectional diameter in relation to the diameter of the intake manifold open end 21, for creating a lower than atmospheric pressure in the interior of venturi section 22 due to the increased velocity of the air flow through the restricted end of manifold 20. This lower than atmospheric pressure, i.e. a partial vacuum, will be utilized to enhance the flow of loose insect eggs from the dispensing device into the spreader as will be hereinafter described in more detail. A tubular connector 23 projects upwardly from the venturi section 22 and communicates with the interior thereof for purposes of connecting, by means of a tubing such as tubing 14 shown in FIG. 1, the venturi section to the dispensing mechanism 10, for purposes to be hereinafter further explained.

The spreader or deflector duct section 24 has a generally flat triangular or "fan" shape with one side 26 being open to form a generally elongated slot-like exhaust opening through which air and loose insect eggs are broadcast from the spreader 12. The apex of the triangular spreader section 24 opposite the open side 26 tapers to an inlet opening that matches the outlet size of the venturi section 22 and is attached thereto. Mounted vertically across the open-slotted end 26 of spreader section 24 are a plurality of vertical deflector tabs 25. The deflector tabs are made of a deformable material, such as sheet metal, such that they may be bent or oriented to create the desired broadcast pattern of the loose insect egg laden air as it is exhausted from the open-slotted end 26 of the spreader 12. In operation, when aircraft 11 has forward motion, air is scooped in by the open end 21 of the manifold and forced through venturi section 22 and into the spreader or deflector section 24.

The air stream is forced to a higher velocity by the "forcing cone" shape of air manifold 20, the air reaching its desired maximum velocity within venturi section 22, and then exits into spreader duct section 24, where the rapidly increasing cross-sectional area of the spreader rapidly lowers the air stream velocity to a much lower velocity at the exhaust exit through the slotted open end 26 in order to achieve greater air dispersion and a larger broadcast pattern of the loose insect eggs.

The loose insect eggs from dispensing apparatus 10 are applied via tubing 14 to the input of the venturi section 22 by means of connector 23. The slight vacuum present in venturi section 22 is applied through connector 23 to tubing 14 for exerting a vacuum pressure on the loose eggs in the dispensing apparatus 10, thus enhancing the gravitationally induced flow of the loose insect eggs from the dispensing apparatus 10, and drawing the eggs into the interior of the venturi section 22. The loose insect eggs are mixed with the air stream as they are drawn into the interior of venturi section 22 and are immediately propelled by the air stream into the spreader or deflector section 24 for broadcast through the open slotted end 26 of the spreader 12 to form the desired broadcast pattern as hereinabove described.

The spreader 12 may be constructed of any suitable material such as fiberglass, plastic or metal. The preferred embodiment shown in FIGS. 2A and 2B is constructed of sheet metal which provides sufficient rigidity and resistance to deformation due to wind stresses while the aircraft is operational. While the description herein has been directed to an aircraft mounted airborne spreader, the spreader could just as well be adapted for attachment to a moving land vehicle and positioned in an elevated posture to discharge and broadcast the loose eggs behind the moving vehicle. A supplementary means of inducing air flow into the spreader other than by virtue of vehicular motion may have to be employed.

Figure 3:
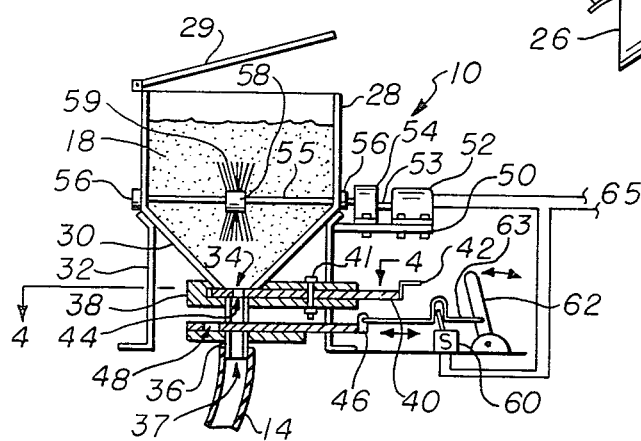
FIG. 3 is a detailed vertical cross-sectional view of one embodiment of the container and metering apparatus for dispensing loose insect eggs to the spreader.
Figure 4:
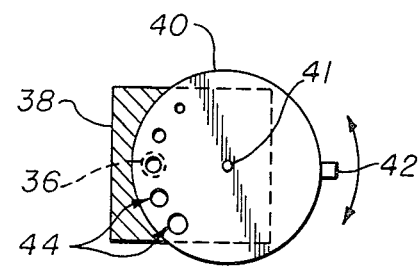
FIG. 4 is a detailed horizontal cross-sectional view of the metering device as taken along lines 4—4 of FIG. 3.

Referring now to FIGS. 3 and 4, the primary embodiment of the dispensing apparatus 10 is shown in greater detail. An elongated container or hopper 28 is shown with lower conical walls 30 forming a "funnel-shaped" bottom portion having an outlet opening 34 in the apex end of the conically shaped section 30. Container 28 is mounted on a suitable mounting bracket 32 which holds and supports container 28 in an upright, rigid position, and is adapted for mounting within the cockpit or fuselage of aircraft 11 or other suitable vehicle. Mounted on the discharge end 36 of the lower conically-shaped section 30 is an orifice plate mounting bracket 38 that has an internal slot for accommodating a variable orifice plate 40. Orifice plate 40 is mounted for limited rotational motion within a slot of bracket 38 by means of a bolt or pivot pin 41 and may manually be rotated by means of a handle 42. A plurality of spaced orifices are disposed adjacent the periphery of orifice plate 40, and have varying sizes for selectively registering a selected orifice size with the outlet opening 37 in cylindrical outlet tube 36 for providing a means of metering the flow rate of the loose insect eggs from the container 28. Since the parasitized host insect egg is typically no longer than one and one-half millimeters in length, and less than 0.33 millimeters in diameter, the orifices 44 can be relatively small and need only vary slightly to make a positive change in the flow rate of the dry, loose eggs through the apex outlet 34 from container 28. The orifices may, of course, be of any predetermined size, but it has been found in practice that a range of orifices from 3/32 inches to 7/32 inches are adequate to provide variations in the flow rate for purposes of adjusting the broadcast spreading of the Trichogramma parasitized host eggs. In practice, it is desired to achieve a 0.1 gram per second flow rate under ideal conditions, but of course, this may have to vary higher or loser depending on the field conditions present. There are approximately 50,000 loose, dry, Trichogramma parasitized host eggs per gram, and with the above-mentioned 0.1 gram per second flow rate, approximately 5,000 Trichogramma parasitized host eggs per second would be metered through orifice plate 40 and into the outlet tube 36 for broadcasting as hereinabove described.

Disposed immediately below orifice plate mounting bracket 38 is a gate support mounting bracket 45 that is adapted to support and guide a sliding gate 46 that has disposed therein a gate opening 48. Gate 46 passes through outlet tube 36, and has one end attached by means of a linkage 63 to a gate actuating handle 62 for "on-off" actuation of gate 46. With the gate shown in its closed position (FIG. 3) all flow of the loose eggs 18 through apex outlet opening 34 and outlet tube 36 is stopped. However, upon actuation of handle 62, gate 46 is opened to permit registration of gate opening 48, and tubing 36 to permit resumption of the free flow of dry, loose insect eggs 18 from container or vessel 28 through opening 34, orifice 44, gate opening 48 and discharge through tube 36 and discharge outlet 37.

A bracket 50 is suitably mounted to the mounting bracket 32 for mounting an electric motor 52, the output drive shaft of which 53 is connected to a reduction gearbox 54. Reducing gearbox 54 drives a shaft 55 that is journaled for rotation within container 28 through bearings 56 disposed in the walls of container 28. Mounted centrally on shaft 55 is a brush 58 having extending flexible bristles 59. Electric motor 52 and reducing gearbox 54 are each suitably mounted to bracket 50 by means of conventional fasteners (not shown). Electric motor 52 is connected to a source of electric power 65 by means of an "off-on" switch 60.

In operation, hopper 28, which may be of any convenient size, was designed to hold 500 grams of loose insect eggs 18. Container 28 may be filled to the desired capacity and lid 29 is closed. Depending on the field conditions, orifice plate 40 is rotated by means of handle 42 to select the desired orifice 44 for controlling the flow rate of the loose eggs from container 28 through the apex opening 34. Once the aircraft is in position, gate actuating handle 62 is moved to open gate 46 and allow the free flow of insect eggs 18 through apex opening 34 from container 28, orifice 44, and gate opening 48 to flow by means of gravity from container 28, through tube 36 into the flexible tubing 14 for application to the spreader 12 as hereinabove described. At the same time, to enhance the flow of loose insect eggs 18 from container 28 and to prevent the loose eggs from sticking together and to container 28, the agitation brush 58 is activated. Switch 60 is thrown to apply electric current from source 65 to motor 52, thus driving brush 58 with its long flexible bristles 59 at a predetermined slow rate of speed, preferably 6-9 rpm, to agitate and continually mix and vibrate the loose eggs 18 within container 28 without damaging the eggs and aiding in the downward movement of the eggs toward the outlet apex opening 34 along the downwardly slanted container sides 30. To terminate the loose insect egg flow from dispensing apparatus 10, switch 60 is actuated to its "off" position, thereby turning off electrical motor 52, and simultaneously actuating lever or handle 62 to close gate 46, thereby shutting off all flow of loose insect eggs from container 28.

Figure 5:
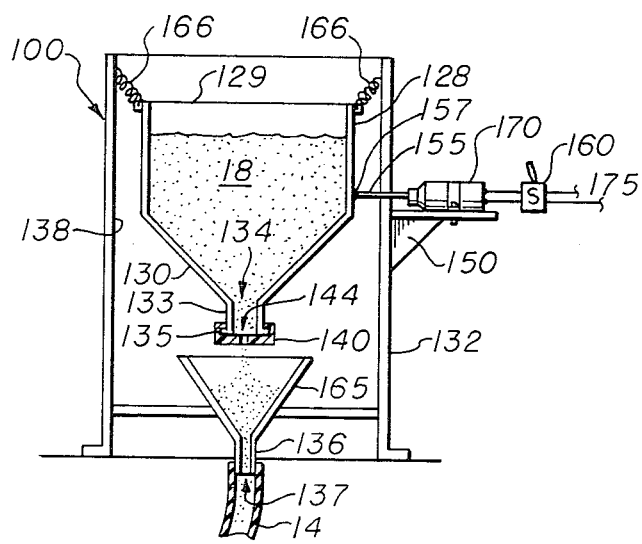
FIG. 5 is a detailed vertical cross-sectional view of a second embodiment of the container and metering means of the present invention.

Referring now to FIG. 5, a second embodiment 100 of the dispensing apparatus is shown. Dispensing apparatus 100 comprises an upright frame or bracket assembly adapted for rigid mounting within the cockpit or fuselage of aircraft 11, as hereinabove described. Frame assembly 132 is adapted for accommodating an elongated container 128 having downwardly sloping conical bottom walls 130 for forming a "funnel-shaped" lower portion having an apex outlet opening 134 that opens into a depending nozzle 133. Nozzle 133 has disposed thereon a flanged rim 135 for accommodating and mating with a flexible orifice cap 140. Orifice cap 140 has disposed therethrough at least one or a plurality of openings or orifices 144 that restrict the flow of loose eggs 18 from the interior of container 128 through apex opening 134. In this way, orifice cap 140 performs a metering function for metering the flow rate of the Trichogramma parasitized host insect eggs 18 from container 128, similarly to the manner in which the orifice plate 40 provided a metering means as hereinabove described.

Container 128 is suspended for limited vertical and horizontal movement within frame assembly 132 by means of suspension springs 166 that are attached to the upper container edge 129 and to the interior wall 138 of bracket assembly 132. Mounted axially below nozzle 133 and orifice cap 140 is a funnel 165 having downwardly sloping conical sides ending in a cylindrical tube section 136 with an outlet opening 137. The flexible tubing 114 that is connected to the spreader apparatus 12 is removably connected to the depending tube portion 136 of funnel 165 for directing the flow of the loose insect eggs 18 from the dispensing apparatus 100 to the spreader 12. Mounted on the side of frame assembly 132 is a bracket 150 to which is attached a vibrator motor 170 by means of any conventional fastening devices (not shown). The vibrator 170 is connected to a source of electrical power 175 through a switch 160. The vibrator shaft 155 is attached to a side wall of container 128 by means of any suitable connection 157, which may be a mechanical linkage, or a suitable adhesive.

In operation, a desired quantity of loose parasitized host eggs 18 are poured into container 128 after the desired metering orifice cap 140 has been selected and mated to the flanged end 135 of nozzle 133. Switch 160 is thrown to actuate vibrator motor 170 and which in turn vibrates container 128 by means of shaft 155 to cause a constant vibration and agitation of the loose eggs 18 within container 128 thereby facilitating their gravity flow through apex opening 134 and orifice opening 144. The loose eggs falling through the orifice cap 140 drop directly into the axially aligned funnel 165 from which they flow through tube 136, exit opening 138 and directly into tubing 14 for application to spreader 12 for broadcasting the loose insect eggs as hereinabove described.

Figure 6:
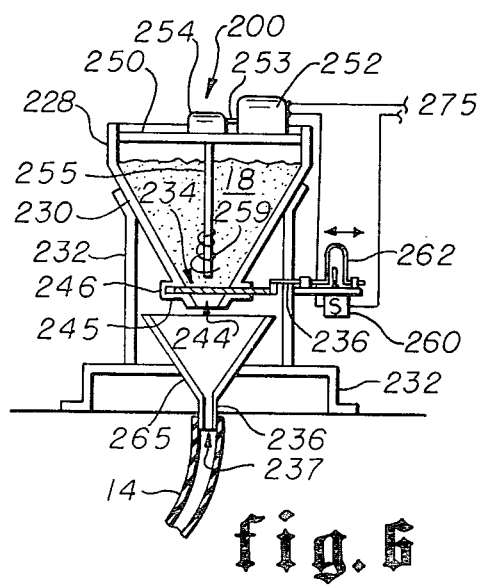
FIG. 6 is a detailed vertical cross-sectional view of another embodiment of the container and metering means of the present invention.

Referring now to FIG. 6, a third embodiment 200 of the dispensing apparatus will be described. Dispensing apparatus 200 comprises a container or hopper 228 having a generally downwardly sloping conically shaped lower portion 230, similar in configuration to container 28 and 128 of the embodiments hereinabove described. Container 228 is rigidly supported by means of a frame or bracket assembly 232 and is adapted for rigid mounting within the cockpit or fuselage of aircraft 11 as hereinabove described. Adjacent the lower end of the slanting section 230 is a gate support bracket 245 that slidably accommodates a gating plate 246. One end of gate 246 is connected by a suitable linkage 263 to a gate-actuating arm or lever 262. Actuation of lever 262 causes the gating plate 246 to slide within the support assembly 245 and open a desired portion of the apex opening 234 from container 228 to determine the outlet opening size and therefore meter the flow rate of the loose insect eggs 18 from container 228. Axially aligned below container 228 is the open end of a funnel-shaped collector 265 having a depending cylindrical tube 236 with an outlet opening 237. Flexible tubing 14, which is connected to the spreader apparatus 12, as hereinabove described, is removably connected to tube 236 for carrying the loose insect eggs from collector 265 to the spreader 12 for broadcasting the loose eggs as hereinabove described. A mounting bracket 250 is disposed in the uppermost portion of container 228 and is fixed therein by any suitable conventional fastening means (not shown). Mounted on bracket 256 is an electric motor 252 the output drive shaft of which is connected to a reducing gearbox 254. The gearbox 254 has an output shaft 255 that extends axially downwardly into container 228 and terminates above gating plate 246 centrally of the apex outlet 234. An agitating means, such as a wire or blade 259 are fixed to the depending end of shaft 255. Electrical motor 252 is connected to a source of electrical power 275 through a switch 260. In operation, handle 262 is actuated to move gating plate 246 to a desired withdrawn position for opening a predetermined portion of the apex outlet 236 from container 228, thus determining the flow rate of the insect eggs from container 228. Switch 260 is thrown for actuating motor 252 which in turn drives shaft 255 through the reduction gearbox 254. Shaft 255 is selected to rotate at a sufficiently low rate of speed, such as 6–9 rpm, that will not injure the loose insect eggs 18, but will create a constant agitation and movement of the eggs in the vicinity of the "gated open" apex opening 234 for allowing the gravity induced eggs to fall from the discharge orifice 244. The loose eggs 18 that fall from the discharge orifice 244 of container 228 fall into the axially aligned collector funnel 265 and thence through tube 236 and outlet 237 into flexible tubing 14 for delivery to the spreader apparatus 12 as hereinabove described.

Numerous variations and modifications may be made in the structure herein described without departing from the present invention. Accordingly, it should be clearly understood that the forms of the invention herein described and shown in the figures of the accompanying drawings are illustrative only and are not intended to limit the scope of the invention.

What is claimed is:

1. Apparatus for airborne release of loose dry live insect eggs from a moving vehicle, comprising a hopper mounted within the vehicle for receiving and holding a limited quantity of the loose eggs in a loose dry condition without crushing the live eggs, the hopper having an inlet opening at the top and downwardly and inwardly slanted sides that terminate in an outlet for discharging the eggs, flow control means cooperating with said hopper outlet for selectively controlling the flow rate of the eggs dispensed from said hopper through said outlet, an elongated air intake manifold mounted externally of said vehicle and having an open end for receiving air flow therethrough, said manifold sides tapering to a restricted outlet end for increasing the velocity of the air leaving said manifold, a cylindrical venturi section axially aligned with said manifold, one end of which is attached to said restricted outlet end of said manifold for receiving said air flow from said manifold, said venturi section having a radial opening disposed therein, the velocity of the air passing through said venturi section from said manifold lowering the air pressure at said radial opening below atmospheric pressure, a length of tubing interconnecting said hopper outlet and said radial opening of said venturi section for creating a pressure differential between the interior of said venturi section and said hopper outlet for forcing the loose dry eggs from said hopper outlet through said flow control means and said tubing into said venturi section for mixing the loose dry eggs in said air flow therein, said pressure differential acting substantially solely as the force for moving the loose dry eggs from said hopper to said venturi section, a generally triangular flattened duct having an open side forming an elongated exhaust slot and a restricted inlet end co-axially aligned with and attached to the exhaust end of said venturi section for receiving said loose eggs carried in said air stream from said venturi section, and a plurality of vertically-oriented spaced deformable deflector tabs fixed to the open outlet end of said exhaust slot for transversely deflecting said loose egg-laden air stream from said outlet slot for broadcasting the loose insect eggs in a desired pattern.

2. The apparatus as described in claim 1, further including agitating means cooperating with said hopper for agitating the loose insect eggs within said hopper for maintaining the eggs in a loose condition.

3. The apparatus as described in claim 2, wherein said agitating means comprises a rotatable shaft disposed laterally through said hopper and journaled therein for rotation, agitator means mounted on said shaft within said hopper for rotation with said shaft to gently agitate the loose eggs adjacent said outlet opening, and drive means connected to said shaft for rotatably driving said shaft and agitator means.

4. The apparatus as described in claim 3, wherein said agitator means comprises a circular brush mounted on said shaft, the bristles of said brush engaging and agitating the loose eggs as said brush rotates.

5. The apparatus as described in claim 3, wherein said driving means comprises
a motor, and
a reduction gearbox connected to the output shaft of said motor and said rotatable shaft for rotating said shaft at a predetermined rotational speed.

6. The apparatus as described in claim 1, wherein said flow control means comprises variable orifice means cooperating with the outlet of said hopper for selectively metering the flow of loose eggs from said outlet.

7. The apparatus as described in claim 6, wherein said variable orifice means comprises
a plate having a plurality of spaced differing-sized orifices disposed therein, and
mounting means for supporting said plate adjacent the hopper outlet and permitting limited movement of the plate for permitting selective registration of one of said orifices in said plate with said hopper outlet opening.

8. The apparatus as described in claim 7, wherein said plate is a circular plate having said spaced orifices disposed proximate the outer peripheral edge thereof, said plate cooperating with said mounting means for rotational movement.

9. The flow control means as described in claim 6, further including gate means cooperating with said hopper outlet for permitting selective closing of said outlet to interrupt the flow of the loose eggs from said hopper.

10. The apparatus as described in claim 9, wherein said gate means comprises
a plate having an orifice disposed in a portion thereof,
mounting means for supporting said plate in transverse relation to said outlet and permitting limited movement of said plate in relation to said outlet, and
actuating means connected to said plate for causing limited selected movement of said plate to register said plate orifice with said outlet to permit loose egg flow, and for moving said plate orifice out of register with said outlet to permit said plate to block said outlet to interrupt loose egg flow.

11. The apparatus as described in claim 2, wherein said agitating means comprises
an upright housing sized to accomodate said hopper,
a plurality of spaced suspension members fixed to the inside of said housing and attached to said hopper for suspending said hopper within said housing and providing limited movement thereof,
vibrator means mounted on said housing, and
a rigid connection fixed to said vibrator means and attached to said hopper for vibrating said suspended hopper for agitating the loose eggs contained therein.

12. The apparatus as described in claim 6, wherein said outlet end of said hopper has a flange disposed about the end thereof and said variable orifice means comprises
a removable cap having disposed therein at least one orifice of a preselected size, said cap having gripping means for mating with said flange of said hopper outlet end for retaining said orifice cap in register with said outlet, and
a funnel mounted below said orifice cap and axially aligned therewith for receiving the metered flow of loose eggs from said hopper through said orifice cap.

13. The apparatus as described in claim 2, wherein said agitating means comprises
a mounting bracket attached across the open end of said hopper inlet,
a rotatable shaft journaled through said mounting bracket vertically into said hopper and having a free end extending downwardly therein,
agitator means mounted adjacent the free end of said shaft proximate said outlet, and
drive means connected to said shaft for rotatably driving said shaft and agitator means.

14. The apparatus as described in claim 13, wherein said agitator means comprises a radially projecting member fixed to said shaft.

15. The apparatus as described in claim 14, wherein said projecting member is an elongated coil of wire fixed to the free end of said shaft and axially disposed thereabout and projecting therefrom.

16. The apparatus as described in claim 15, wherein said driving means comprises
a motor mounted on said bracket, and
a reduction gearbox mounted on said bracket and interconnected between the output shaft of said motor and said rotatable shaft for rotating said shaft at a predetermined rotational speed.

17. The apparatus as described in claim 6, wherein said variable orifice means comprises
a plate member,
mounting means for supporting said plate member for limited movement in transverse relation to said outlet opening, and
actuating means connected to said plate for causing limited movement thereof for selectively withdrawing one end of said plate from said outlet opening for permitting flow of the loose eggs through said outlet opening at a selected flow rate.

18. A method of airborne release of loose dry live insect eggs, comprising the steps of
inducing a flow of the eggs from a container receiving and holding the eggs,
controlling the flow rate of the eggs discharged from said container,
inducing an air current flow,
creating an air pressure differential with the air pressure in said container for forceing the eggs into said air current flow,
mixing the eggs in said air current flow, and
broadcasting the eggs entrained in said air current in a desired pattern.

19. The method as described in claim 18 further including the step of agitating the loose insect eggs prior to controlling the flow thereof.

* * * * *